United States Patent [19]

Steplewski et al.

[11] Patent Number: 4,607,009
[45] Date of Patent: Aug. 19, 1986

[54] LEWIS BLOOD GROUP PHENOTYPE ASSAY

[75] Inventors: Zenon Steplewski, Strafford; Hilary Koprowski; Meenhard Herlyn, both of Wynnewood, all of Pa.

[73] Assignee: The Wistar Institute, Philadelphia, Pa.

[21] Appl. No.: 532,891

[22] Filed: Sep. 16, 1983

[51] Int. Cl.⁴ ............... G01N 33/544; G01N 33/541; C12N 15/00; C12N 5/00
[52] U.S. Cl. ................................. 435/7; 435/172.2; 435/240; 935/96; 935/99; 935/102; 935/103; 935/106; 935/110; 436/513; 436/528; 436/540; 436/548; 424/11; 424/85
[58] Field of Search ............... 935/96, 99, 102, 103, 935/106, 110; 435/172.2, 7, 240; 436/512, 513, 528, 540, 548, 813; 424/11, 85

[56] References Cited

PUBLICATIONS

Herlyn et al., "Colorectal Carcinoma—Specific Antigen: Detection by Means of Monoclonal Antibody," *Proc. Natl. Acad. Sci., USA*, vol. 76, pp. 1438–1442 (Mar. 1979).

Young et al., "Characterization of Monoclonal Ab Specific for the Lewis a Human Blood Group Determinant," *J. of Biol. Chem.*, vol. 258, pp. 4890–4894 (Apr. 1983).

Rohr et al., "Production of Mouse Monoclonal Antibodies to Blood Group Active Oligosaccharide", *Fed. Proc.*, 42(3): 1983 (Apr.), p. 432, Abt: 815.

Race & Sanger, Blood Groups in Man, pp. 323–349 (6th Ed., 1975).

Koprowski et al, The Lancet, Jun. 12, 1982, pp. 1332–1333.

Brockhaus et al, J. Biol. Chem., 256, pp. 13223–13225.

Blaszczyk et al, Second Annual Congress for Hybridoma Research, Abstract.

Journal of Immunological Methods, 62 (1983), pp. 73–78.

Magnani, Second Annual Congress for Hybridoma Research, Abstract.

*Primary Examiner*—Lionel M. Shapiro
*Assistant Examiner*—Elizabeth C. Weimar
*Attorney, Agent, or Firm*—Banner, Birch, McKie & Beckett

[57] ABSTRACT

An assay for determining the Lewis blood group of a patient consists of testing a body sample for the presence of Lewis$^a$ and Lewis$^b$ antigens. Monoclonal antibodies specific for either of these antigens are employed which do not cross-react with other related antigens, such as the H blood antigen. Body samples which may be tested include: saliva, serum, urine, and paraffin-embedded tissue samples. Hybridoma cell lines and the antibody compositions they produce specific for these antigens are provided for use in the assay.

22 Claims, 1 Drawing Figure

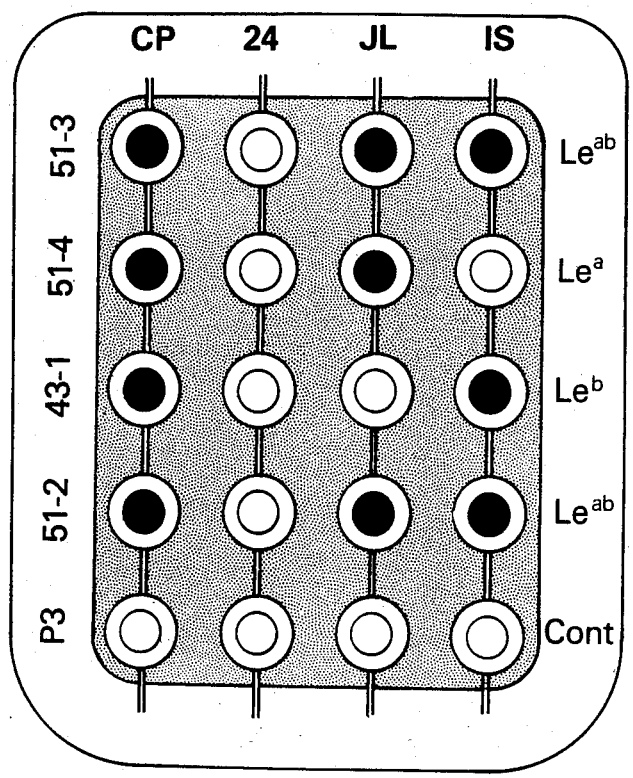

LEWIS BLOOD GROUP PHENOTYPE ASSAY

TECHNICAL FIELD

The present invention is directed to an assay useful in the determination of the Lewis blood group phenotype of a test subject.

BACKGROUND OF THE INVENTION

The Lewis (Le) blood group antigens, a and b, were originally defined by two anti-sera designated anti-Le$^a$ and anti-Le$^b$. See Andersen (1948), *Acta Path. Microbiol. Scand.* 25: 728; Mourant, (1946) *Nature* 158: 237. Based on these anti-sera, four Lewis phenotypes were distinguished: Le$^{a+b+}$, Le$^{a-b-}$, Le$^{a+b-}$, and Le$^{a-b+}$. An individual, therefore, may possess one Lewis antigen (Le$^{a+b-}$ or Le$^{a-b+}$), both Lewis antigens (Le$^{a+b+}$), or neither Lewis antigen (Le$^{a-b-}$). See generally, R. Race and R. Sanger, *Blood Groups In Man* Chp. 9 (6th ed. 1975).

Le$^a$ and Le$^b$ antigens occur as a terminal sugar sequence of glycolipids and glycoproteins in human saliva, serum, erythrocytes and other body fluids and tissues. The Le$^a$ antigen contains the terminal sugar sequence:

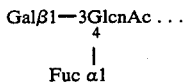

and the Le$^b$ antigen contains the terminal sequence:

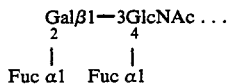

The Le$^b$ antigen, as can be seen, contains the same terminal sequence as the Le$^a$ antigen with the addition of a fucosyl residue.

It is important to screen for Lewis blood group phenotypes prior to blood transfusions. If the donor's Lewis phenotype does not match the receipent's, a haemolytic transfusion reaction can result.

The Lewis blood group antigens are also related to the gastrointestinal cancer-associated antigen (GICA), which is present on cells of adenocarcinoma of the colon, stomach, or pancreas. GICA's antigenic terminal is sialylated lacto-N-fucopentaose II, which is a sialylased Le$^a$ antigen. It is believed that an individual must be able to synthesize the Lewis terminal sugar sequences in order to express GICA, the same enzymes being involved. See, e.g., Koprowski et al., Lancet, June 12, 1982, at 1332–1333. It is desirable, therefore, to know whether an individual is Le$^{a-b-}$ (approximately 5% of the population) if a diagionistic assay for the presence of GICA is negative.

Assays for Lewis phenotypes employ anti-sera obtained from humans or animals. Several problems exist with anti-sera. First, anti-sera are by necessity polyclonal in nature. Most anti-Le$^a$ sera contain some weak anti-Le$^b$ when obtained from Le$^{a-b-}$ donors. Precipitating and agglutinating anti-Le$^a$ sera has been obtained from animals, such as, chickens, rabbits and goats. Anti-Le$^b$ sera often contains anti-H antibodies which can result in a false indication of Le$^{b+}$. The H antigen is a precursor of the Lewis antigens. See R. Race and R. Sanger, supra, 338–39.

Murine hybridomas have been reported that produce monoclonal antibodies directed against the Le$^b$ antigen. Brockhaus et al., (1981) *J. Biol. Chem.* 256: 13223. Some of these monoclonal antibodies, however, have been found to exhibit cross-specificity with the H blood antigen.

It would be desirable, therefore, to develop an assay that employs monoclonal antibodies that selectively bind either the Le$^a$ antigen or the Le$^b$ antigen, but not both. Furthermore, it would be desirable to employ monoclonal antibodies that do not cross-type for other blood group antigens.

SUMMARY OF THE INVENTION

It is an object of the present invention to provide an assay that determines Lewis blood group phenotype.

It is also an object of the present invention to provide an assay employing monoclonal antbodies that determines Lewis blood group phenotype.

Another object of the present invention is to provide an assay for Lewis blood group phenotype that employs monoclonal antibodies that selectively identify Le$^a$ antigen, but cross-type with neither Le$^b$ antigen nor other blood group antigens.

Yet another object of the present invention is to provide an assay for Lewis blood group phenotype that employs monoclonal antibodies that selectively identify Le$^b$ antigen, but cross-type with neither Le$^a$ antigen nor other blood group antigens.

Still another object of the present invention is to provide hybridomas and monoclonal antibodies useful in an assay for Lewis blood group phenotypes.

These and other objects are achieved by one or more of the following embodiments of the present invention.

In one embodiment, the present invention provides a method of determining Lewis blood group phenotype comprising providing a test sample selected from the group consisting of human tissue and human body fluid, and determining whether monoclonal test antibodies selectively bind antigens in said test sample, said monoclonal test antibodies corresponding to monoclonal antibodies produced by (a) fused cell hybrid ATCC HB 8324 and (b) a fused cell hybrid selected from the group consisting of ATCC HB 8325 and ATCC HB 8326.

In another embodiment, the present invention provides a method of determining Lewis blood group phenotype comprising testing a sample selected from the group consisting of human saliva and human blood for the presence of antigenic determinants selectively bound by monoclonal antibodies produced by fused cell hybrid ATCC HB 8324 and a fused cell hybrid selected from the group consisting of ATCC HB 8325 and ATCC HB 8326.

Yet another embodiment of the present invention is a method of determining Lewis blood group phenotype comprising: (a) providing at least two solid support members contacted with a human saliva sample, said solid support member having the ability to immobilize glycolipids or glycoproteins; (b) contacting a first said solid support member with monoclonal test antibodies corresponding to monoclonal antibodies produced by fused cell hybrid ATCC HB 8324; (c) contacting a second said solid support member with monoclonal test antibodies corresponding to monoclonal antibodies produced by a fused cell hybrid selected from the group consisting of ATCC HB 8325 and ATCC HB 8326; (d)

after said monoclonal test antibody-contacting steps, contacting each of said solid support members with indicator antibodies that selectively bind said monoclonal test antibodies; and (e) determining whether said indicator antibodies selectively bind to monoclonal test antibodies on said solid support members.

Additional embodiments of the present invention include the fused cell hybrids ATCC HB 8322, ATCC HB 8323, ATCC HB 8324, ATCC HB 8325 and ATCC HB 8326, as well as the monoclonal antibodies produced by the said fused cell hybrids.

BRIEF DESCRIPTION OF THE FIGURE

The FIGURE is an example of a typical reaction tray with test samples in an enzyme-linked immunoabsorbent assay preformed according to the present invention.

DETAILED DESCRIPTION OF THE INVENTION

The present invention provides an effective method for determining the Lewis blood phenotype of an individual. The assay of the present invention is fast, accurate and, in one embodiment, does not require the drawing of blood from a patient. The assay takes advantage of novel fused cell hybrids that produce monoclonal antibodies, as well as the antigenic determinants of those antibodies.

$Le^a$ and $Le^b$ antigens are found in various human body fluids and tissues that contain glycolipids or glycoproteins. Examples include, but are not limited to, blood, saliva, urine, erythrocytes and other tissue or fluids. Withdrawing a glycoprotein- or glycolipid-containing test sample, therefore, provides the substrate for the present assay. The preferred test sample is human saliva since it does not require penetration of the skin. Furthermore, Lewis blood group antigens are expressed in the saliva whether the test subject is a secretor or nonsecretor phenotype. The present assay, however, can readily be employed with, for example, blood, urine or other samples. Paraffin-embedded tissue samples can even be employed since glycolipids are not destroyed by fixatives such as formalin.

The preferred method of determining the presence of the $Le^a$ and $Le^b$ antigens employs certain monoclonal test antibodies that correspond to antibodies produced by particular fused cell hybridomas. These fused cell hybrids produce monoclonal antibodies that selectively bind Lewis blood group antigens at particular antigenic determinants. The hybridomas were produced by immunizing individual mice with either of the colon carcinoma cell lines SW 1116 on SW 1222 described in Leibovitz et al., (1976) *Cancer Res.* 36: 4562. Spleen cells from the immunized mice were fused with mouse myeloma P 3X63 Ag8 and hybridomas recovered according to methods known in the art. See, e.g., Koprowski, et al., U.S. Pat. No. 4,196,265.

Several hybridomas useful in the present invention have been developed by the above method. Fused cell hybrid ATCC HB 8324 produces monoclonal antibody CO-514 ($IgG_3$ isotype) which selectively binds the lacto-N-fucopentaose II active terminal sequence of the $Le^a$ antigen. Fused cell hybrids ATCC HB 8325 and ATCC HB 8326 secrete monoclonal antibody CO-431 and CO-301, respectively, (IgM isotype) which selectively bind the lacto-N-difucohexaose I active terminal sequence of the $Le^b$ antigen. Unlike the monoclonal antibodies from hybridoma 1116NS-10 reported in Brockhaus et al., (1981) *J. Biol. Chem.* 256: 13223, these antibodies do not cross-type for other blood group antigens, such as the H antigen. Fused cell hybrids ATCC HB 8322 and ATCC HB 8323 produce monoclonal antibodies CO-512 ($IgG_3$ isotype) and CO-513 ($IgG_3$ isotype), respectively, which selectively bind both $Le^a$ and $Le^b$ antigens. The above fused cell hybrids were deposited on July 28, 1983 with the American Type Culture Collection (ATCC), 12301 Parklawn Drive, Rockville, Md. 20852. A solution containing these monoclonal antibodies substantially free of other antibodies can be obtained by collecting supernatant from growing cultures of the fused cell hybrids.

The preferred monoclonal test antibodies employed in the present invention are those produced by the above hybridomas. Monoclonal antibodies that correspond to these preferred test antibodies can also be employed. As used herein, a monoclonal test antibody will correspond to the antibody produced by a fused cell hybrid when a test antibody selectively bound to an antigen blocks the selective binding of the antibody produced by the fused cell hybrid, indicating that the antibodies share the same antigenic determinant. An antibody that corresponds to the fused cell hybrid antibody can be readily determined, for example, by a competitive binding assay. It is not necessary that the monoclonal test antibodies employed in the present assay be mouse antibodies. Rat, hamster, rabbit and human antibodies are only some of the types of antibodies that could also be used.

The monoclonal test antibodies described above are readily employed in the preferred method of determining the presence of Lewis blood group antigens $Le^a$ and $Le^b$ in a test sample. A preferred test sample is saliva. Glycolipid or glycoprotein from the saliva can be immobilized on a solid support member with the ability to absorb glycolipids or glycoproteins. Any solid support member known in art may be employed. Preferably, the solid support member is plastic (e.g., polystyrene, polypropylene or polyvinyl). By merely placing such a plastic bead momentarily in the mouth of a test subject, glycolipids or glycoproteins are immobilized on its surface.

The presence of the Lewis blood group antigens on the solid support (or in any other test sample) can be readily determined, for example, by contacting the solid support (or sample) with the monoclonal test antibodies. At a minimum, the test sample should be contacted with a monoclonal test antibody that selectively binds $Le^a$ antigen and another monoclonal test antibody that selectively binds $Le^b$ antigen. It is also desirable as a control, but not necessary, to contact a test sample with a monoclonal test antibody that selectively binds both $Le^a$ and $Le^b$ antigens to confirm results indicating $Le^{a-b-}$ individuals.

The presence of $Le^a$ or $Le^b$ antigens, and thus Lewis phenotype, is determined by an assay that indicates whether monoclonal test antibodies selectively bind these antigens in a test sample. Various binding assay techniques are known in the art. See, e.g., U.S. Pat. No. 4,380,580; U.S. Pat. No. 4,375,972; U.S. Pat. No. 4,376,110; U.S. Pat. No. 4,376,165; U.S. Pat. No. 3,791,932; U.S. Pat. No. 3,654,090; U.S. Pat. No. Re. 31,006. Generally, these assays envolve "tagging" either the monoclonal test antibody or an antibody that selectively binds the monoclonal test antibody (indicator antibodies). The test sample, which preferably contains antigen that has been immobilized, is then either (a) contacted with tagged test monoclonal antibodies, or (b) contacted first by untagged monoclonal test antibodies followed by contact with tagged indicator antibodies. Detection of the tag associated with the test sample indicates that monoclonal test antibodies have selectively bound an antigenic determinant in the test sample.

Various tags are known in the art, including radioisotopes (radioimmunoassays), enzymes (ELISA or enzyme-linked immunoabsorbant assay) and flourescent compounds (immunofluorescence). Other methods for determining the binding of antibodies to antigens are well known in the art, for example, precipitin reactions, radial immunodiffusion, immunoelectrophoresis, agglutination and rosette formation. See, e.g., B. D. Davis et al., *Microbiology* 306–332, 335 (3rd ed. 1980); *Monoclonal Antibodies* 376–402 (R. H. Kennett, T. J. McKearn and K. B. Bechtol eds. 1980); David et al., (1974) *Biochemistry* 13: 1014–1021; *radioimmunoassay Methods* (Kirkham and Hunter eds. 1970); Hunter et al., (1962) *Nature* 144: 945; U.S. Pat. No. 3,940,475; U.S. Pat. No. 3,867,517; U.S. Pat. No. 3,645,090.

In some assays, it may be desirable to immobilize either the test or indicator antibodies. Any of the common supports used in immunoassays may be employed. They include, but are not limited to, filter paper and plastic beads or vessels (e.g., polyvinyl, polystyrene, polypropylene, etc.). Polysaccharides polymers may also be used to bind the antibodies. See, e.g., U.S. Pat. No. 3,645,852.

A preferred assay is a radioimmunoassay which is well known in the art. See, e.g., C. W. Parker, *Radioimmunoassay of Biologically Active Compounds* (1976). A particularly preferred assay, however, is an enzyme-linked immunoabsorbent assay (ELISA). See, e.g., U.S. Pat. No. 3,791,932; U.S. Pat. No. 3,654,090; U.S. Pat. No. Re. 31,006. Such an assay can be readily performed in, for example, a physican's office in only a few minutes employing simplified equipment and avoiding radioisotopes. The particular parameters employed in the assays can vary widely with the particular radioimmunoassay or ELISA employed. Optimal conditions can be readily established by those of average skill in the art. For example, it has been found that when saliva is employed it can be diluted up to 100,000-fold and remain a suitable substrate in the assay.

The following examples are provided for illustrative purposes only. They are not intended to limit the scope of the invention which is defined solely by the claims.

EXAMPLE I

A 1 ml saliva sample was collected from 60 individuals of both sexes. Test subjects ranged in age from 25 to 75 years. Saliva samples were inactivated by heating for 30 minutes at 85° C. in a water bath. The samples were then diluted 1:4 in phosphate-buffered saline (PBS) and stored at −20° C. until the assay was run.

Immediately prior to the assay, saliva samples were diluted 1:20 (or as specified in Table II). Polystyrene beads (Precision Plastic Ball Co., Chicago, Ill., 5 beads/test subject) were incubated with the saliva samples (200 ul/bead) and then washed with 1% gelatin in 0.01M sodium borate (pH 8.0) for 1 hour at ambient temperature. The washed beads were then placed in a reaction tray containing 5 wells for each test subject. Supernatant from growing cell cultures containing fused cell hybrids ATCC HB 8324 ($Le^a$), ATCC HB 8325 ($Le^b$), ATCC HB 8322 ($Le^{ab}$), ATCC HB 8323 ($Le^{ab}$) and mouse myeloma cell P 3X63 Ag8 (control) were added to different wells containing saliva samples from test subjects (5 wells/test subject). The beads were allowed to incubate with the cell culture supernatants for 1 hour at room temperature and then washed 3 times in PBS containing 0.05% bovine serum albumin (BSA).

The washed beads were then incubated with $^{125}$I-labelled affinity-purified rabbit anti-mouse F(ab')$_2$ immunoglobulin at $1 \times 10^5$ cpm/bead for 30 minutes at room temperature. The beads were then washed 3 times with 0.5% BSA in PBS and counted.

Table I indicates the results obtained in the above radioimmunoassay. The assay indicates that test subject CP is $Le^{a+b+}$, test subject 24 is $Le^{a-b-}$, test subject JL is $Le^{a+b-}$, and test subject IS is $Le^{a-b+}$. Table II shows that the saliva samples of $Le^{a+b-}$ and $Le^{a-b+}$ individuals can be diluted up to 100,000 times with clearly positive selective binding demonstrated by the four monoclonal antibodies. Saliva of the $Le^{a-b-}$ individual did not selectively bind the monoclonal antibodies at any of the dilutions tested. Table III shows the proportion of various Lewis blood group phenotypes found among the 60 test subjects.

TABLE I

BINDING OF ANTI-LEWIS ANTIBODIES TO SALIVA SAMPLES AS DETECTED IN RIA$^a$

| Antibody | | Binding (cmp) of saliva samples | | | |
|---|---|---|---|---|---|
| Code | Specificity | CP | 24 | JL | IS |
| CO-513 | $Le^{ab}$ | 9,860 | 480 | 9,530 | 12,010 |
| CO-514 | $Le^a$ | 10,780 | 33 | 10,790 | 350 |
| CO-431 | $Le^b$ | 4,490 | 320 | 690 | 11,090 |
| CO-512 | $Le^{ab}$ | 10,580 | 180 | 10,060 | 12,710 |
| P3 × 63 Ag8 | Control | 452 | 426 | 453 | 481 |

$^a$Input 100,000 cmp per bead. Values represent cmp per single bead from 2 consecutive assays under the same conditions.

TABLE II

LEVELS OF Le ANTIGENS IN SALIVA SAMPLES AS DEFINED BY MONOCLONAL ANTIBODIES DIRECTED AGAINST $Le^a$ (CO-514) OR $Le^b$ (CO-431) HAPTENS

| Saliva samples | | Binding of antibodies (cpm)$^a$ at saliva dilutions | | | | | |
|---|---|---|---|---|---|---|---|
| Code | phenotype | 20 | 50 | 100 | 1,000 | 10,000 | 100,000 |
| 49 | $Le^{(a+b-)}$ | 10,800 | 10,000 | 9,500 | 4,300 | 1,800 | 400 |
| 93 | $Le^{(a-b+)}$ | 12,350 | 11,810 | 8,750 | 5,300 | 1,980 | 900 |
| 44 | $Le^{(a-b-)}$ | 550 | 600 | 430 | 420 | 440 | 480 |

$^a$Input 100,000 cpm per bead.

TABLE III

DISTRIBUTION OF LEWIS PHENOTYPES IN THE SALIVA FROM 60 INDIVIDUALS

| Number of individuals typed as: | | | | |
|---|---|---|---|---|
| $Le^{a+b+}$ | $Le^{a-b-}$ | $Le^{a+b-}$ | $Le^{a-b+}$ | Total |
| 1(1.6)$^a$ | 4(6.6) | 12(20.0) | 43(71.6) | 60 |

$^a$In parenthesis - % of total. $Le^{a+b+}$ reacted with all 4 antibodies. $Le^{a-b-}$ did not react with any of the 4 antibodies. $Le^{a+b-}$ did not react with antibody CO-431. $Le^{a-b+}$ did not react with antibody CO-514.

EXAMPLE II

The present assay was also performed using an enzyme-linked immunoabsorbent assay employing a peroxidase-antiperoxidase (PAP) system instead of the $^{125}$I-labelled rabbit anti-mouse antibody.

In the PAP assay, the polystyrene beads, after incubation with saliva, were incubated with the test monoclonal antibodies in the reaction trays as in Example I and then exposed to biotinylated anti-mouse antibodies (biotin-avidin immunoperoxidase kit, Vector Labs, Burlingame, Calif.) for 30 minutes at ambient temperature.

The beads were then washed 3 times with PBS, incubated with Avidin DH-Biotinylated Horseradish Peroxidase H for 30 minutes at ambient temperature and again washed 3 times with PBS. The peroxidase substrate (5 mg diaminobenzidene, 10 ul 30% $H_2 O_2$, 100 ul 1M immidiazole in 10 ml of 0.1M Tris buffer, pH 7.6) was then added to the wells in the reaction trays. Positive beads were indicated by clear, dark brown staining after incubation for 5-10 minutes.

The FIGURE shows a typical pattern of reactivity for the saliva samples of the four test subjects of Table I. In the FIGURE, 51-2, 43-1, 51-4 and 51-3 indicate the monoclonal antibodies produced by fused cell hybridomas ATCC HB 8322, ATCC HB 8325, ATCC HB 8324 and ATCC HB 8323, respectively. P3 indicates the control wells where supernatant from the mouse myeloma culture P 3×63 Ag8 was added. The FIGURE shows that the Lewis blood group phenotypes for test subjects CP, 24, JL and IS are $Le^{a+b+}$, $Le^{a-b-}$, $Le^{a+b-}$ and $Le^{a-b+}$, respectively. These results agree with the radioimmunoassay of Example I.

While several specific examples of an assay within the scope of the present invention have been provided, variations on the above procedures are readily apparent to those in the art. The present invention, therefore, is to be limited only by the scope of the appended claims.

We claim:

1. A method of determining Lewis blood group comprising contacting a test sample selected from the group consisting of human tissue and human body fluid, with monoclonal antibodies, under conditions which permit the formation of antigen-antibody complexes and determining the presence or absence of said antigen-antibody complexes, said monoclonal antibodies binding to the same antigenic determinants as monoclonal antibodies produced by (a) fused cell hybrid ATCC HB 8324 and (b) a fused cell hybrid selected from the group consisting of ATCC HB 8325 and ATCC HB 8326.

2. The method of claim 1 wherein said test sample is selected from the group consisting of saliva and serum.

3. The method of claim 1 wherein said test sample is saliva.

4. The method of claim 1 further comprising determining the presence or absence of said antigen-antibody complexes wherein said monoclonal antibodies binding to the same antigenic determinants as monoclonal antibodies selected from the group consisting of monoclonal antibodies produced by fused cell hybrid ATCC HB 8322 and ATCC HB 8323.

5. The method of claim 2 further comprising determining the presence or absence of said antigen-antibody complexes wherein said monoclonal antibodies binding to the same antigenic determinants as monoclonal antibodies selected from the group consisting of monoclonal antibodies produced by fused cell hybrid ATCC HB 8322 and ATCC HB 8323.

6. The method of claim 3 further comprising determining the presence or absence of said antigen-antibody complexes wherein said monoclonal antibodies binding to the same antigenic determinants as monoclonal antibodies selected from the group consisting of monoclonal antibodies produced by fused cell hybrid ATCC HB 8322 and ATCC HB 8323.

7. A method of determining Lewis blood group phenotype comprising contacting a sample selected from the group consisting of human saliva and human blood with monoclonal antibodies under conditions which permit the formation of antigen-antibody complexes and determining the presence or absence of said antigen-antibody complexes, wherein said monoclonal antibodies are produced by fused cell hybrid ATCC HB 8324 and a fused cell hybrid selected from the group consisting of ATCC HB 8325 and ATCC HB 8326.

8. The method of claim 7 wherein the means by which the presence or absence of said antigen-antibody complexes is determined is a radioimmunoassay.

9. The method of claim 7 wherein the means by which the presence or absence of said antigen-antibody complexes is determined is an enzyme-linked immunoabsorbent assay.

10. A method of determining Lewis blood group phenotype comprising:
    (a) providing at least two solid support members contacted with a human saliva sample, said solid support members having the ability to immobilize glycolipids or glycoproteins;
    (b) contacting a first said solid support member with monoclonal test antibodies binding to the same antigenic determinants as monoclonal antibodies produced by fused cell hybrid ATCC HB 8324, under conditions which permit the formation of antigen-antibody complexes;
    (c) contacting a second said solid support member with monoclonal test antibodies binding to the same antigenic determinants as monoclonal antibodies produced by a fused cell hybrid selected from the group consisting of ATCC HB 8325 and ATCC HB 3826, under conditions which permit the formation of antigen-antibody complexes;
    (d) after said monoclonal test antibody-contacting steps, contacting each of said solid support members with indicator antibodies that selectively bind said monoclonal test antibodies under conditions which permit the formation of antigen-antibody-antibody complexes; and
    (e) determining the presence or absence of said antigen-antibody-antibody complexes on said solid support member.

11. The method of claim 10 wherein said step (e) comprises a method selected from the group consisting of a radioimmunoassay and an enzyme-linked assay.

12. The method of claim 10 wherein a third saliva-contacted solid support member is contacted with a monoclonal test antibody binding to the same antigenic determinants as antibodies produced by a fused cell hybrid selected from the group consisting of fused cell hybrids ATCC HB 8322 and ATCC HB 8323 under conditions which permit the formation of antigen-antibody complexes.

13. The fused cell hybrid ATCC HB 8322.
14. The fused cell hybrid ATCC HB 8323.
15. The fused cell hybrid ATCC HB 8324.
16. The fused cell hybrid ATCC HB 8325.
17. The fused cell hybrid ATCC HB 8326.
18. Monoclonal antibodies produced by the fused cell hybrid ATCC HB 8322.
19. Monoclonal antibodies produced by the fused cell hybrid ATCC HB 8323.
20. Monoclonal antibodies produced by the fused cell hybrid ATCC HB 8324.
21. Monoclonal antibodies produced by the fused cell hybrid ATCC HB 8325.
22. Monoclonal antibodies produced by the fused cell hybrid ATCC HB 8326.

* * * * *

UNITED STATES PATENT AND TRADEMARK OFFICE
CERTIFICATE OF CORRECTION

PATENT NO. : 4,607,009
DATED : August 19, 1986
INVENTOR(S) : Zenon Steplewski et al It is certified that error appears in the above—identified patent and that said Letters Patent is hereby corrected as shown below:

At Column 3, line 51, "on" should be "or";

At Column 8, line 31, "ATCC HB 3826" should be "ATCC HB 8326".

Signed and Sealed this

Twenty-fourth Day of February, 1987

*Attest:*

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,607,009
DATED : August 19, 1986
INVENTOR(S) : Steplewski, et al.

It is certified that error appears in the above-identified patent and that said Letters Patent is hereby corrected as shown below:

Please insert the following paragraph in the specification before the heading Technical Field in column 1, line 3:

--The U.S. Government has a paid-up license in this invention and the right in limited circumstances to require the patent owner to license others on reasonable terms as provided for by the terms of grant number CA 21124 awarded by the National Institutes of Health.--

Signed and Sealed this

Fifteenth Day of June, 1993

Attest:

MICHAEL K. KIRK

*Attesting Officer*     *Acting Commissioner of Patents and Trademarks*